US005667383A

United States Patent [19]
Mendoza et al.

[11] Patent Number: 5,667,383
[45] Date of Patent: Sep. 16, 1997

[54] DISPOSABLE DENTAL PROPHYLAXIS HANDPIECE

[75] Inventors: José L. Mendoza, Rancho Cordova; Philip Theodore Lingman, Cotati; William Richard Maclay, Sr., Los Gatos, all of Calif.

[73] Assignee: Denticator International, Inc., Sacramento, Calif.

[21] Appl. No.: 294,736

[22] Filed: Aug. 23, 1994

[51] Int. Cl.⁶ .................................................. A61C 1/05
[52] U.S. Cl. ........................... 433/132; 415/141; 415/904
[58] Field of Search ................................. 433/114, 125, 433/126, 132; 415/140, 141, 904; 418/154, 268

[56] References Cited

U.S. PATENT DOCUMENTS

| Re. 24,391 | 11/1957 | McFadden | 451/295 |
|---|---|---|---|
| 263,814 | 9/1882 | Schmitz | 433/112 |
| 969,378 | 9/1910 | Krause | 418/268 |
| 1,343,115 | 6/1920 | Current | 418/266 |
| 1,601,397 | 9/1926 | Kochendarfer | 418/137 |
| 1,999,488 | 4/1935 | Swisher et al. | 433/128 |
| 2,017,881 | 10/1935 | Wiseman | 433/166 |
| 2,025,779 | 12/1935 | Roelke | 433/128 |
| 2,033,662 | 3/1936 | Witt | 433/130 |
| 2,128,157 | 8/1938 | Monnier et al. | 415/34 |
| 2,135,933 | 11/1938 | Blair | 433/166 |
| 2,203,974 | 6/1940 | Weinhardt | 418/154 |
| 2,226,145 | 12/1940 | Smith | 15/29 |
| 2,300,828 | 11/1942 | Goldenberg | 433/166 |
| 2,315,016 | 3/1943 | Shotton | 433/133 |
| 2,328,270 | 8/1943 | Greenberg | 74/56 |
| 2,463,118 | 3/1949 | Moore | 418/137 |
| 2,586,968 | 2/1952 | MaClay | 418/43 |
| 2,684,035 | 7/1954 | Kemp | 418/153 |
| 2,789,352 | 4/1957 | Wiseman | 433/166 |
| 2,836,877 | 6/1958 | Hannahan | 27/24 |
| 2,933,046 | 4/1960 | McCray | 418/154 |

(List continued on next page.)

FOREIGN PATENT DOCUMENTS

| 646193 | 6/1937 | Germany. | |
|---|---|---|---|
| 803306 | 7/1949 | Germany. | |
| 102433 | 5/1951 | New Zealand | 433/132 |
| 12584 | 3/1903 | Sweden. | |
| 2154283 | 9/1985 | United Kingdom | 418/268 |
| 2 209 284 | 5/1989 | United Kingdom. | |

OTHER PUBLICATIONS

Denticator; Product Brochure; 1990; entire brochure.
Oralsafe; Advertisement for oralsafe disposable handpiece; Dentistry Today Trade Journal; Aug., 1992; entire advertisement.

(List continued on next page.)

Primary Examiner—Stephen R. Funk
Attorney, Agent, or Firm—Bernhard Kreten

[57] ABSTRACT

A disposable dental prophylaxis handpiece 10 is provided having a rotor 90 with vanes 92 pivotably connected thereto. The handpiece 10 includes an entrance 30 for elevated pressure fluid and an outlet 40 for discharge of the fluid after contacting the rotor 90. The elevated pressure fluid passes from the entrance 30, into a high pressure chamber 80. The high pressure chamber 80 is in contact with inlet ports 74 accessing a cylinder 72 within the handpiece 10. The cylinder 72 supports the rotor 90 with a rotational axis M of the rotor 90 off center with respect to a central axis N of the cylinder 72. The elevated pressure fluid causes the rotor 90 and an attached output shaft 97 to rotate. This in turn pauses a prophylaxis cup 160, coupled to the output shaft 97, to rotate. The rotor 90 includes a trunk 24 with a plurality of posts 93 extending therefrom and with vanes 92 connected to the posts 93 through hinges 94. The vanes 92 can pivot from a first position collapsed against the trunk 24 to a second position spaced away from the trunk 24. The vanes 92 thus can contact a cylindrical wall 78 of the cylinder 72 while the rotor 90 rotates. Exhaust ports 76 are spaced from the inlet ports 74 and provide communication with a low pressure chamber 82 which exhausts low pressure fluid to the outlet 40.

20 Claims, 7 Drawing Sheets

U.S. PATENT DOCUMENTS

| | | | |
|---|---|---|---|
| 2,937,444 | 5/1960 | Kern | 433/132 |
| 3,043,274 | 7/1962 | Quackenbush | 173/221 |
| 3,054,355 | 9/1962 | Neely | 418/154 |
| 3,163,934 | 1/1965 | Wiseman | 433/115 |
| 3,192,922 | 7/1965 | Winkler | 433/132 |
| 3,229,369 | 1/1966 | Hoffmeister et al. | 433/105 |
| 3,309,965 | 3/1967 | Weickgenannt | 433/132 |
| 3,376,825 | 4/1968 | Burnett . | |
| 3,421,224 | 1/1969 | Brehm et al. | 433/132 |
| 3,477,793 | 11/1969 | Kitagawa | 415/36 |
| 3,510,229 | 5/1970 | Smith | 415/141 |
| 3,719,440 | 3/1973 | Snider | 418/266 |
| 3,727,313 | 4/1973 | Graham | 433/125 |
| 3,740,853 | 6/1973 | Brahler | 433/112 |
| 3,855,704 | 12/1974 | Booth | 433/101 |
| 3,856,432 | 12/1974 | Campagnuolo et al. | 416/45 |
| 3,877,574 | 4/1975 | Killick | 206/368 |
| 3,942,392 | 3/1976 | Page, Jr. et al. | 433/132 |
| 3,955,284 | 5/1976 | Balson | 433/132 |
| 3,987,550 | 10/1976 | Danne et al. | 433/84 |
| 4,040,311 | 8/1977 | Page, Jr. et al. | 433/132 |
| 4,053,983 | 10/1977 | Flatland | 433/133 |
| 4,171,571 | 10/1979 | Gritter | 433/120 |
| 4,182,041 | 1/1980 | Girard | 433/115 |
| 4,185,386 | 1/1980 | Nordin et al. | 433/82 |
| 4,248,589 | 2/1981 | Lewis | 433/80 |
| 4,259,071 | 3/1981 | Warden et al. | 433/166 |
| 4,266,933 | 5/1981 | Warden et al. | 433/82 |
| 4,365,956 | 12/1982 | Bailey | 433/115 |
| 4,392,779 | 7/1983 | Bloemers et al. | 415/141 |
| 4,465,443 | 8/1984 | Kardén | 418/43 |
| 4,540,337 | 9/1985 | Olsen | 415/141 |
| 4,693,871 | 9/1987 | Geller | 433/116 |
| 4,767,277 | 8/1988 | Buse | 416/241 |
| 4,795,343 | 1/1989 | Choisser | 433/116 |
| 4,842,516 | 6/1989 | Choisser | 433/132 |
| 4,846,638 | 7/1989 | Pahl et al. | 418/268 |
| 4,863,344 | 9/1989 | Stefanini | 415/141 |
| 4,929,180 | 5/1990 | Moreschini | 433/166 |
| 4,941,828 | 7/1990 | Kimura | 433/114 |
| 5,020,994 | 6/1991 | Huang | 433/126 |
| 5,028,233 | 7/1991 | Witherby | 433/125 |
| 5,040,978 | 8/1991 | Falcon et al. | 433/125 |
| 5,062,796 | 11/1991 | Rosenberg | 433/82 |
| 5,094,615 | 3/1992 | Bailey | 433/88 |
| 5,120,220 | 6/1992 | Butler | 433/125 |
| 5,156,547 | 10/1992 | Bailey | 433/125 |
| 5,163,825 | 11/1992 | Oetting | 418/268 |

OTHER PUBLICATIONS

SmartPractice; Advertisement for a smart angle prophy angle; entire advertisement.

Dental Products Report, "Disposable Handpiece", Nov. 1992, p. 96.

Diversified Dental Supply, Inc., Advertisement for Disposable High Speed Hand Pieces, entire advertisement.

The National Magazine for Dental Hygiene Professionals, Product Report, "Prophy Cups", Jan. 1992, p. 38.

Dental Products Report, New Products, "Prophy Cups", Jan. 1992, p. 30.

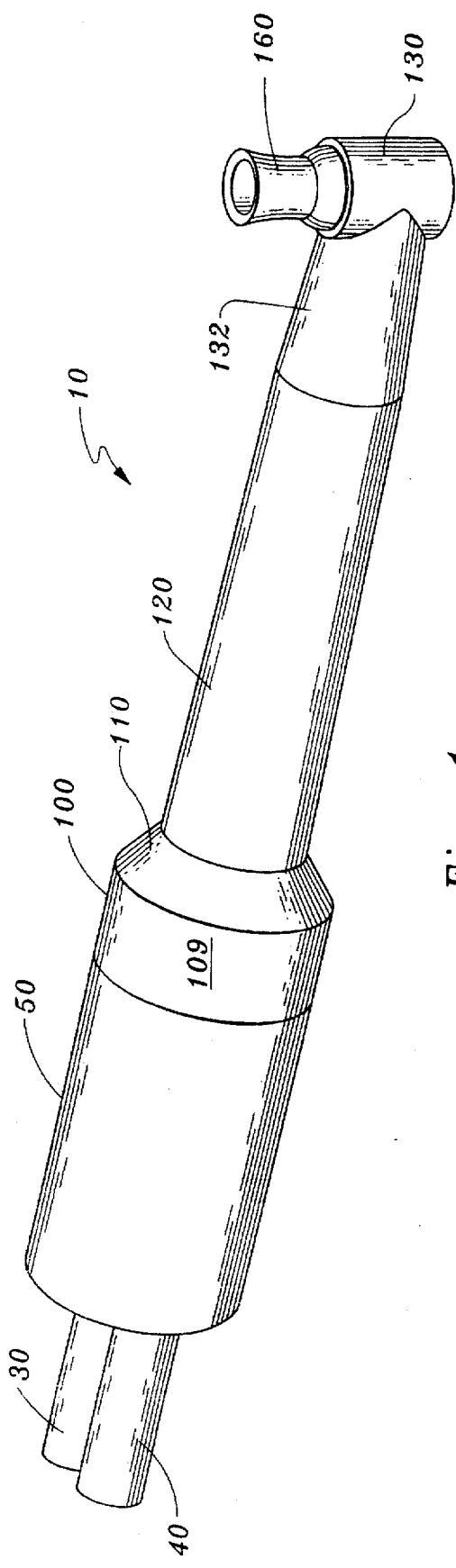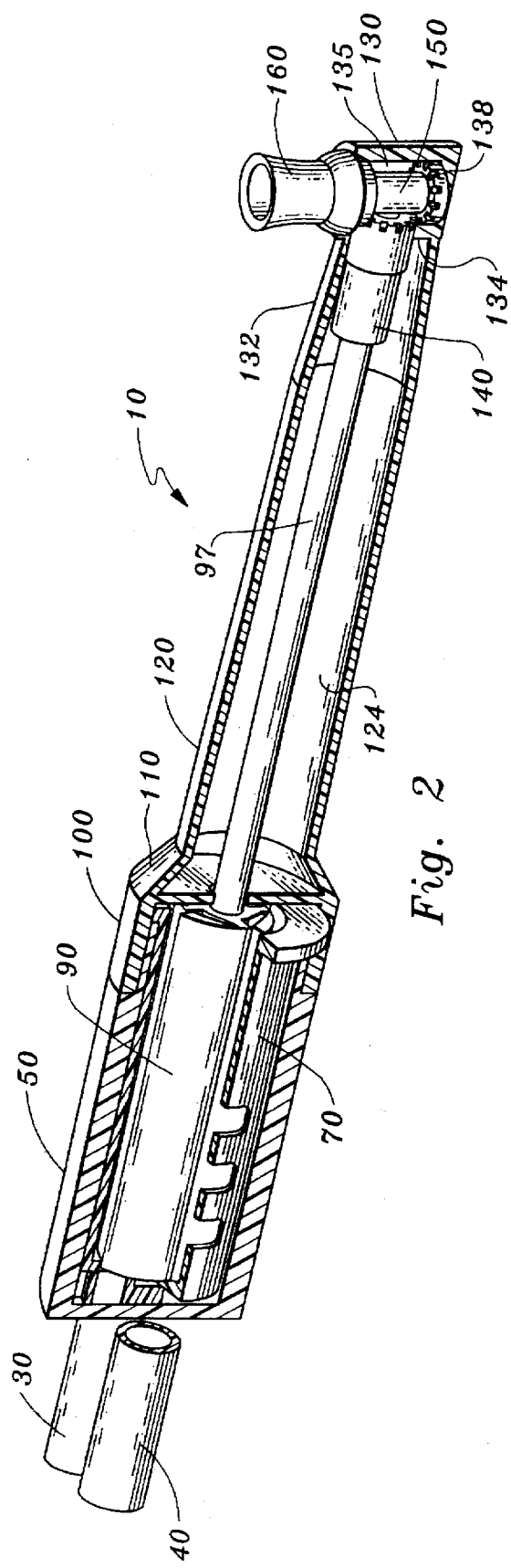

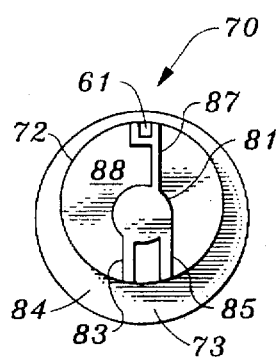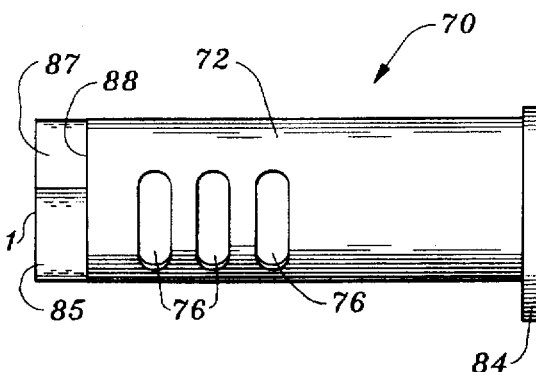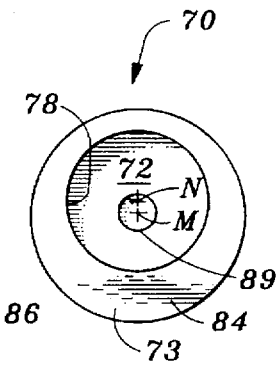
Fig. 7　　　Fig. 6　　　Fig. 8
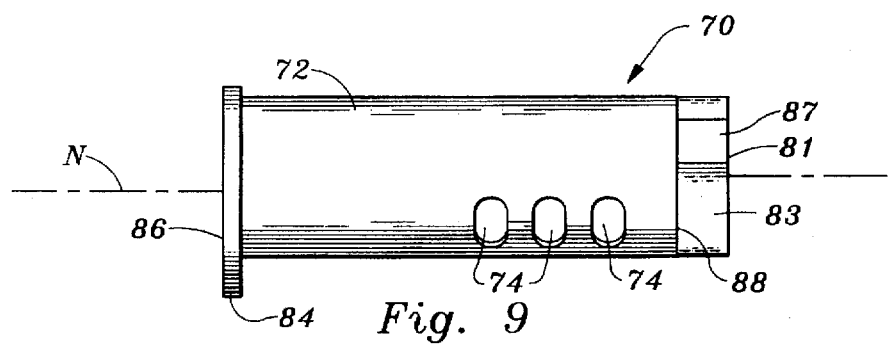
Fig. 9
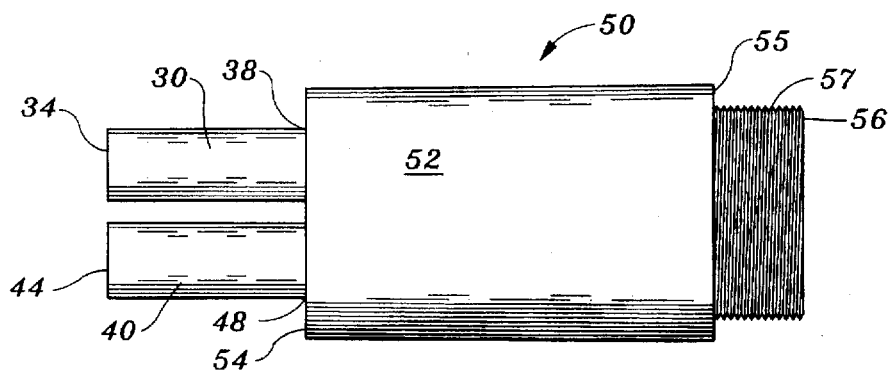
Fig. 10
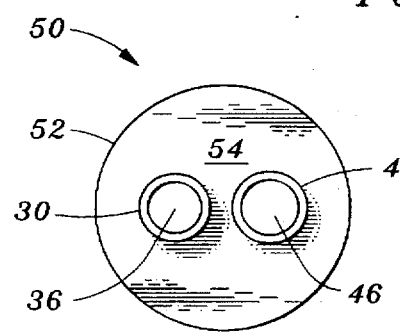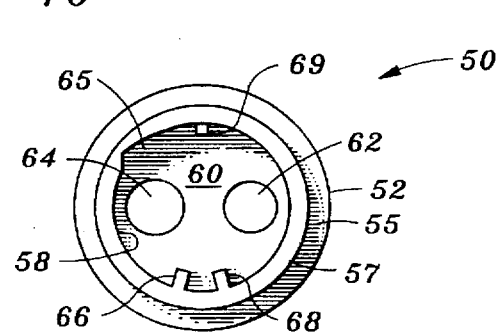
Fig. 11　　　Fig. 12

DISPOSABLE DENTAL PROPHYLAXIS HANDPIECE

FIELD OF THE INVENTION

This invention generally relates to disposable dental prophylaxis handpieces for performing dental prophylaxis procedures which utilize elevated pressure gases or liquid to generate rotational motion of a prophylaxis cup. More specifically, this invention relates to hand held small diameter dental prophylaxis handpieces with high torque and relatively low speed when unloaded which include a rotor having dynamic vanes which move relative to the rotor.

BACKGROUND OF THE INVENTION

In recent years, the dental operatory has been identified as a possible location where contagious diseases can be transferred between individuals. This information has led to a variety of new products to minimize any possibility that diseases be transferred to an individual while that individual is receiving dental treatment. One procedure of concern in possibly transmitting contagious diseases is dental prophylaxis. During prophylaxis, a dental practitioner removes plaque, tartar, stains and other debris accumulating on the individual's teeth. This prophylaxis procedure is performed with a rotating prophylaxis cup which often includes an abrasive paste supported therein until it is applied to the teeth of the individual. The rotating prophylaxis cup is supported by a housing which also includes a fluid driven motor to cause the prophylaxis cup to rotate.

Handpieces are known in the art which are specifically provided to rotatably support the prophylaxis cup for performing dental prophylaxis. These handpieces include a housing which is sized to be easily grasped by a user and includes a fluid driven motor therein which has an output shaft coupled to the prophylaxis cup. The motor is coupled to a source of elevated pressure air which causes a rotor of the motor to rotate.

Dental prophylaxis handpieces have been identified as one possible site where contamination between individuals can occur, resulting in the transmission of communicable disease. To thwart such contamination, it is generally advised that practitioners thoroughly sterilize the handpieces between use. Such sterilization procedures are time-consuming and often result in damage to the handpiece, diminishing the handpiece's useful life. Hence, some practitioners resort to other, less effective, methods of sterilization or must purchase additional handpieces, increasing the cost to deliver this preventative dental maintenance procedure.

The known dental prophylaxis handpieces include fluid driven motors with dynamic rotors which rely on high pressure compressible fluids to operate. The rotor includes flat vanes which slide away from and toward a geometric center of the rotor. The rotor is located asymmetrically within a cylinder such that air passing from an inlet to an outlet within the cylinder causes the rotor to rotate in only one direction. The vanes slide away from and toward a rotational axis of the rotor as the rotor rotates. Because such sliding flat vane rotors contact a wall of the cylinder, friction exists which determines a maximum free speed of the rotor for a given air pressure. Such motors also exhibit relatively high torque at lower speeds than high velocity air motors.

While such sliding flat vane rotors are generally effective, the prophylaxis procedure requires higher torque at still lower speeds than those obtainable with flat sliding vane rotors. The current solution of gearing the output shaft to obtain desired speeds is too complex to facilitate economical disposability. Additionally, at start up flat sliding vane rotors require some form of system to extend the vanes away from the rotor before centrifugal forces are sufficient to maintain the vanes against a surrounding cylindrical wall. Finally, such flat sliding vane rotors must be formed with multiple pieces and to precise tolerances to ensure that the vanes can effectively slide within slots in the rotor. Such complexity makes single use of the handpiece economically prohibitive.

Accordingly, a need exists for a dental prophylaxis handpiece which has high torque at low speeds but which is easily manufactured and has vanes which extend readily when the motor is started. Such a handpiece would facilitate effective prophylaxis and yet could be economically discarded after a single use.

The following prior art reflects the state of the art of which applicant is aware and is included herewith to discharge applicant's acknowledged duty to disclose relevant prior art. However, it is respectfully submitted that none of these prior art devices teach singly, nor render obvious when considered in any conceivable combination, the nexus of the instant invention as especially claimed hereinafter.

| INVENTOR | PATENT NO. | ISSUE DATE |
|---|---|---|
| Schmitz | 263,814 | September 5, 1882 |
| Swisher et al | 1,999,488 | April 30, 1935 |
| Wiseman | 2,017,881 | October 22, 1935 |
| Roelke | 2,025,779 | December 31, 1935 |
| Monnier, et al. | 2,128,157 | August 23, 1938 |
| Blair | 2,135,933 | November 8, 1938 |
| Smith | 2,226,145 | December 24, 1940 |
| Goldenberg | 2,300,828 | November 3, 1942 |
| Shotton | 2,315,016 | March 30, 1943 |
| Greenberg | 2,328,270 | August 31, 1943 |
| Wiseman | 2,789,352 | April 23, 1957 |
| McFadden | Re. 24,391 | November 12, 1957 |
| Kern | 2,937,444 | May 24, 1960 |
| Wiseman | 3,163,934 | January 5, 1965 |
| Winkler | 3,192,922 | July 6, 1965 |
| Hoffmeister, et al. | 3,229,369 | January 18, 1966 |
| Brehm, et al. | 3,421,224 | January 14, 1969 |
| Smith | 3,510,229 | May 5, 1970 |
| Graham | 3,727,313 | April 17, 1973 |
| Brahler | 3,740,853 | June 26, 1973 |
| Booth | 3,855,704 | December 24, 1974 |
| Campagnuolo, et al. | 3,856,432 | December 24, 1974 |
| Killick | 3,877,574 | April 15, 1975 |
| Balson | 3,955,284 | May 11, 1976 |
| Danne, et al. | 3,987,550 | October 26, 1976 |
| Flatland | 4,053,983 | October 18, 1977 |
| Gritter | 4,1,71,571 | October 23, 1979 |
| Girard | 4,182,041 | January 8, 1980 |
| Lewis | 4,248,589 | February 3, 1981 |
| Warden et al. | 4,259,071 | March 31, 1981 |
| Melcher | 4,261,536 | April 14, 1981 |
| Warden et al. | 4,266,933 | May 12, 1981 |
| Bailey | 4,365,956 | December 28, 1982 |
| Karden | 4,465,443 | August 14, 1984 |
| Geller | 4,693,871 | September 15, 1987 |
| Buse | 4,767,277 | August 30, 1988 |
| Choisser | 4,795,343 | January 3, 1989 |
| Choisser | 4,842,516 | June 27, 1989 |
| Stefanini | 4,863,344 | September 5, 1989 |
| Moreschini | 4,929,180 | May 29, 1990 |
| Kimura | 4,941,828 | July 17, 1990 |
| Huang | 5,020,994 | June 4, 1991 |
| Witherby | 5,028,233 | July 2, 1991 |
| Falcon et al. | 5,040,978 | August 20, 1991 |
| Rosenberg | 5,062,796 | November 5, 1991 |
| Bailey | 5,094,615 | March 10, 1992 |
| Butler | 5,120,220 | June 9, 1992 |
| Bailey | 5,156,547 | October 20, 1992 |

-continued

FOREIGN PATENT DOCUMENTS

| DOCUMENT NUMBER | DATE | NAME | CLASS | SUB-CLASS* | FILING DATE |
|---|---|---|---|---|---|
| 646,193 (Germany) | 06/1937 | Dürhager | 30b | 202 | 5/1937 |
| 102,433 (New Zealand) | 05/1951 | Callaghan | 433 | 132 | |
| GB 2 209 284-A Fed. Republic of Germany 646,193 | 05/1989 June, 1937 | Kalsha | A61C | 1/05 | 07/1988 |

OTHER PRIOR ART (Including Author, Title, Date, Pertinent Pages, Etc.)

Lewis, Advertisement for Oralsafe Disposable Handpiece Dentistry Today, August 1992.

Denticator; Product Brochure; 1990; entire brochure.

Oralsafe; Advertisement for Oralsafe Disposable Handpiece; Dentistry Today Trade Journal; August, 1992; entire advertisement.

SmartPractice; Advertisement for a smart angle prophy angle; entire advertisement.

Dental Products Report, "Disposable Handpiece", November 1992, page 96.

Diversified Dental Supply, Inc., Advertisement for Disposable High Speed Hand Pieces, entire advertisement.

The National Magazine for Dental Hygiene Professionals, Product Report, "Prophy Cups", January 1992, page 38.

Dental Products Report, New Products, "Prophy Cups", January 1992, page 30.

Oralsafe; Advertisement for Oralsafe disposable handpieces; Impact, The Newsmagazine of the Academy of General Dentistry, December 1992; entire advertisement.

The Oralsafe handpiece brochure teaches a disposable dental handpiece. This invention is distinguishable from the teachings of Oralsafe in that, inter alia, this invention provides output speeds appropriate for prophylaxis, rather than higher speeds for drilling, and provides a pivoting vane rotor not taught by Oralsafe.

The patent to Smith teaches a one-way pump with an impeller having blades connected to the impeller through a flexible web portion which allows the blades to be pivoted in one direction but not the other. The present invention is distinguishable from Smith for several reasons. Inter alia, shaft power is provided for an output shaft instead of pumping fluid through a system. Also, the vanes of this invention contact a cylinder wall and the rotor of this invention is offset within the cylinder within which it resides.

The patent to Stefanini teaches a centrifugal pump having impeller blades which are pivoted to rotate between two extreme positions. The present invention is distinguishable from the pump taught by Stefanini in that, inter alia, the present invention provides a fluid reaction device producing shaft rotation instead of fluid pumping. Also, the vanes of this invention contact a cylindrical wall surrounding the vanes, and the rotor of the present invention is oriented offset with respect to a center of the cylinder within which it rotates.

The remainder of the prior art diverge even more starkly from the present invention than the prior art specifically distinguished above.

SUMMARY OF THE INVENTION

The disposable dental prophylaxis handpiece of this invention includes a housing sized to be graspable by a hand of a user and which can be easily maneuvered into a mouth of an individual. The housing supports a fluid reaction device therein which is coupled to a prophylaxis cup such that when elevated pressure air is supplied to the fluid reaction device, the prophylaxis cup is caused to rotate for performing prophylaxis procedures.

The fluid reaction device utilizes fluid, such as air under elevated pressure, to cause the prophylaxis cup to rotate. The device includes a rotor with vanes extending therefrom. An output shaft is coupled to the rotor which drives the prophylaxis cup. The rotor is supported within a cavity which allows rotation of the rotor therein. Inlet ports and exhaust ports pass into the cavity at either an end or side thereof to allow fluid under elevated pressure to enter the cavity and reduced pressure fluid to exit the cavity. The inlet ports are coupled to a source of elevated pressure fluid outside the housing.

The rotor is supported so that a rotational axis of the rotor is spaced from a central axis of symmetry of the cavity. Thus, the rotor is oriented off-center within the cavity. The vanes of the rotor are pivotably attached to the rotor such that the vanes can contact the cavity wall at all times by pivoting away from and toward the rotor as the rotor rotates. The pivoting vanes deter fluid from passing around the rotor without rotor rotation. The pivoting vanes also generate friction for the rotor, acting as a governor by keeping the rotor from exceeding a maximum free speed for the device. The pivoting vanes are exposed to the driving fluid at all times, maximizing a reaction surface for the high energy fluid. The pivoting vanes provide the rotor with a greater radius on one side of the rotor than on an opposite of the rotor. This difference increases a torque imparted by the rotor to the output shaft and the prophylaxis cup. The device has a small enough diameter to easily be held by a dental practitioner within a mouth of an individual.

OBJECTS OF THE INVENTION

Accordingly, it is a primary object of the present invention to provide a dental prophylaxis handpiece exhibiting low speed and high torque characteristics.

It is another object of the present invention to provide a dental prophylaxis handpiece including a rotor which is caused to rotate by elevated pneumatic fluid pressure and which causes a prophylaxis cup to rotate.

Another object of the present invention is to provide a dental prophylaxis handpiece having a rotor formed from low cost easily machined materials.

Another object of the present invention is to provide a dental prophylaxis handpiece formed from injection moldable plastic materials.

It is another object of the present invention to provide a dental prophylaxis handpiece including a fluid reaction device which can produce torque without rotation.

It is another object of the present invention to provide a dental prophylaxis handpiece including a fluid reaction device having a rotor with vanes which pivot with respect to a trunk of the rotor.

Another object of the present invention is to provide a dental prophylaxis handpiece including a fluid reaction device with a rotor having vanes which have a first position adjacent a trunk of the rotor and a second position spaced from a trunk of the rotor manufactured to be biased toward the second position.

Another object of the invention is to provide a dental prophylaxis handpiece which is disposable.

Another object of the present invention is to provide a dental prophylaxis handpiece exhibiting a substantially constant free speed when unloaded and powered with a constant fluid pressure differential.

It is another object of the present invention to provide a dental prophylaxis handpiece including a fluid reaction device including a rotor with vanes which contact a wall surrounding the cavity without requiring precise dimensional tolerances for the vanes.

It is another object of the present invention to provide a dental prophylaxis handpiece including a fluid reaction device which minimizes cooling by inhibiting significant adiabatic expansion of drive fluid utilized therein.

Another object of the present invention is to provide a dental prophylaxis handpiece which is lightweight and can be held in the hand of a user.

Another object of the present invention is to provide a disposable prophylaxis handpiece with an alternative to the air motor featuring a rotor with radially sliding vanes by providing a fluid reaction device featuring a rotor with pivoting vanes.

Another object of the present invention is to provide a dental prophylaxis handpiece including an air motor with a rotor oriented offset within a cavity to increase a torque produced by the rotor.

Another object of the present invention is to provide a dental prophylaxis handpiece which is self-starting.

Another object of the present invention is to provide a dental prophylaxis handpiece that is easy to make and assemble.

Another object of the present invention is to provide a dental prophylaxis handpiece having a fluid reaction device with a rotor including a trunk, hinges and vanes which can be all formed integrally together or can be formed separately.

Another object of the present invention is to provide a dental prophylaxis handpiece which delivers high power and high torque with a small diameter.

Viewed from a first vantage point it is the object of the present invention to provide a disposable dental prophylaxis handpiece for imparting rotation to a prophylaxis cup, comprising in combination: a housing; a fluid reaction device receiving fluid as input and having a rotating shaft as output, the fluid reaction device including a rotor having a substantially rigid trunk, a plurality of vanes, and a means to pivotably attach said vanes to said trunk, and a hollow cavity, said cavity including means to inlet fluid into said cavity, means to exhaust fluid out of said cavity, and means to rotatably support said trunk of said rotor within said cavity; and said rotating shaft output coupled to said rotor such that when fluid enters said cavity, said shaft is caused to rotate, said shaft including means to impart rotation to the prophylaxis cup.

Viewed from a second vantage point it is the object of the present invention to provide a method for utilizing fluid to cause a dental prophylaxis device to rotate, including the steps of: forming a rotor to include a trunk and a plurality of vanes; connecting each vane through a hinge to the trunk, the hinge allowing each said vane to pivot with respect to the trunk between a first collapsed position and a second extended position; orienting the rotor within a hollow cavity; providing an inlet fluid port passing into the cavity; providing an outlet fluid port passing into the cavity; coupling the rotor to a means to transmit rotational energy from the rotor to the dental prophylaxis device; coupling the inlet fluid port to a source of fluid; and directing fluid from the source of fluid through the inlet fluid ports and into contact with the vanes of the rotor, causing the rotor and the dental prophylaxis device to rotate.

Viewed from a third vantage point it is the object of the present invention to provide a dental prophylaxis handpiece including a fluid reaction device having a substantially constant velocity rotational output for imparting rotation to a prophylaxis cup, comprising in combination: a rotor having a trunk, vanes and hinge means between said trunk and said vanes to pivot said vanes between a first position and a second position; a wall surrounding said rotor; said first position defined by said vanes collapsed adjacent said trunk with a portion of said vanes abutting said wall; said second position defined by said vanes pivoted away from said trunk with a portion of said vanes abutting said wall; an inlet passing through said wall coupled to a source of fluid; an outlet passing through said wall; and an output means interposed between said rotor and the prophylaxis cup.

These and other objects will be made manifest when considering the following detailed specification when taken in conjunction with the appended drawing figures.

BRIEF DESCRIPTION OF THE DRAWINGS

FIG. 1 is a perspective view of the dental prophylaxis handpiece of this invention as assembled.

FIG. 2 is a perspective view of this invention as shown in FIG. 1 with an exterior housing, sleeve and insert partially cut-away to reveal interior details.

FIG. 6 is a side view of an insert portion of this invention.

FIG. 7 is a rear view of the insert portion of this invention.

FIG. 8 is a front view of an insert portion of this invention.

FIG. 9 is an opposite view of the insert portion of this invention.

FIG. 10 is a top view of a housing portion of this invention.

FIG. 11 is a rear view of that which is shown in FIG. 10.

FIG. 12 is a front view of that which is shown in FIG. 10.

DESCRIPTION OF PREFERRED EMBODIMENTS

Figure 3:
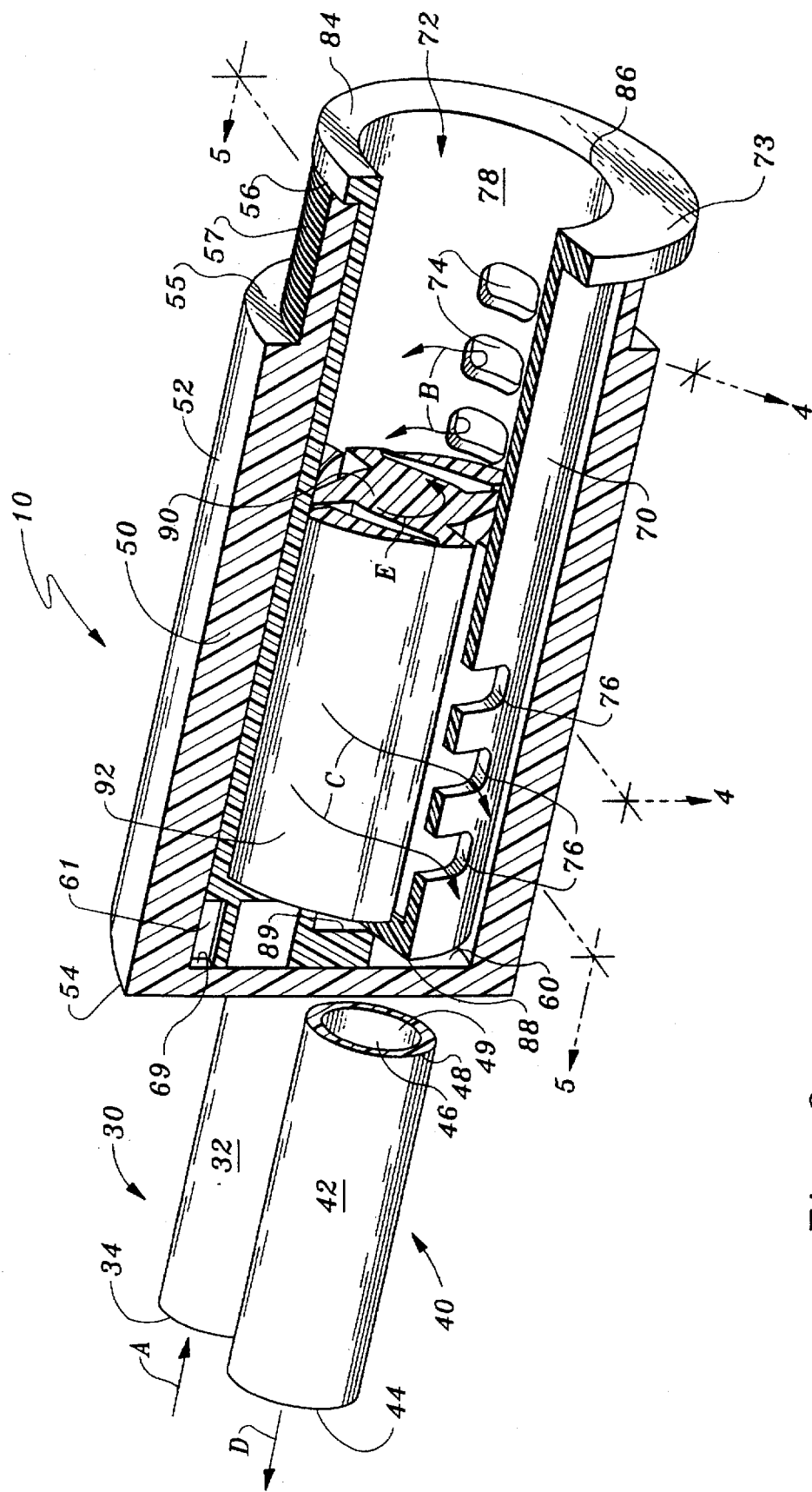
FIG. 3 is a perspective view of that which is shown in FIG. 1 with portions thereof cut away to reveal interior details such as how the fluid passes through the device.

Referring to the drawings, wherein like reference numerals represent like parts throughout the various drawing figures, reference numeral 10 is directed to a disposable dental prophylaxis handpiece. The handpiece 10 (FIG. 1)

receives high pressure fluid through an entrance 30 along arrow A, and discharges the fluid through an outlet 40 along arrow D. A rotor 90 (FIG. 2) is addressed by the high pressure fluid in a manner causing an output shaft 97 connected to the rotor 90 to rotate, in turn rotating a prophylaxis cup 160.

Figure 5:
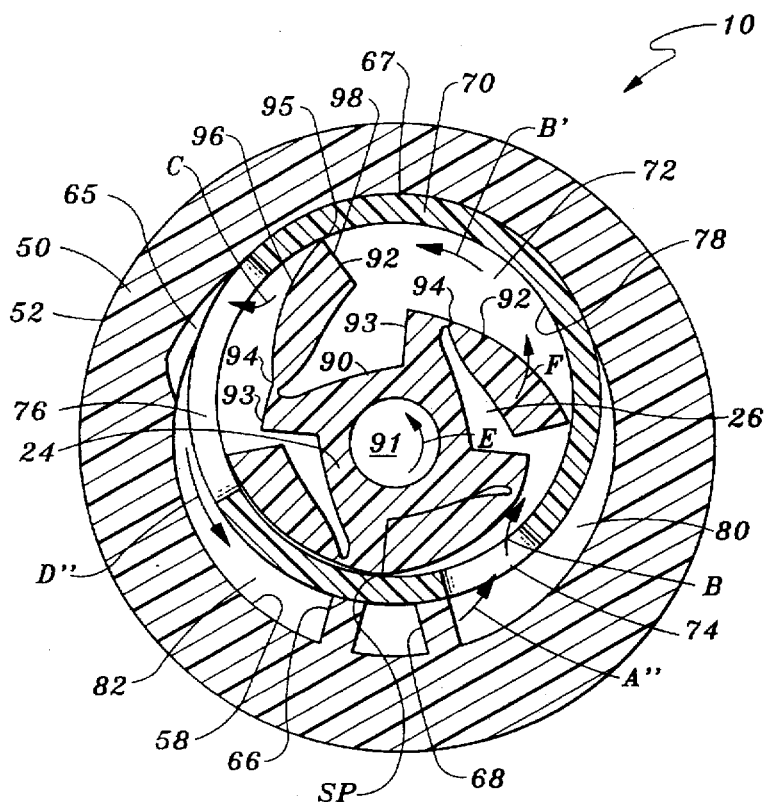
FIG. 5 is a sectional view taken along line 5—5 of FIG. 3.

In essence, and with reference to FIGS. 1 through 3, the handpiece 10 includes the following elements. The entrance 30 and outlet 40 are coupled to a housing 50 in a manner allowing high pressure fluid to pass into and out of the housing 50 through the entrance 30 and outlet 40. An insert 70 is nested within an interior of the housing 50. The insert 70 includes a cylinder 72 which has inlet ports 74 and exhaust ports 76 passing therethrough. The insert 70 is sized smaller than an interior of the housing 50 such that a high pressure chamber 80 and a low pressure chamber 82 are oriented between the insert 70 and the housing 50 (FIG. 5). A first divider wall 66 and second divider wall 68 divide the high pressure chamber 80 and the low pressure chamber 82.

Figure 13:
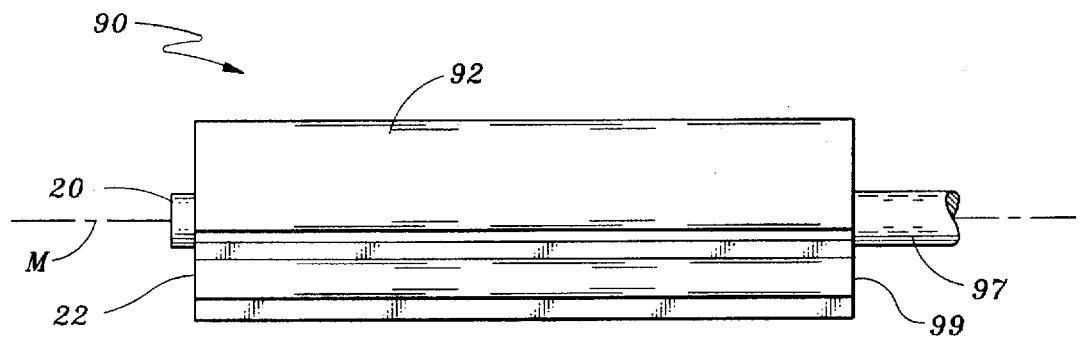
FIG. 13 is a side view of a rotor portion of this invention.
Figure 15:
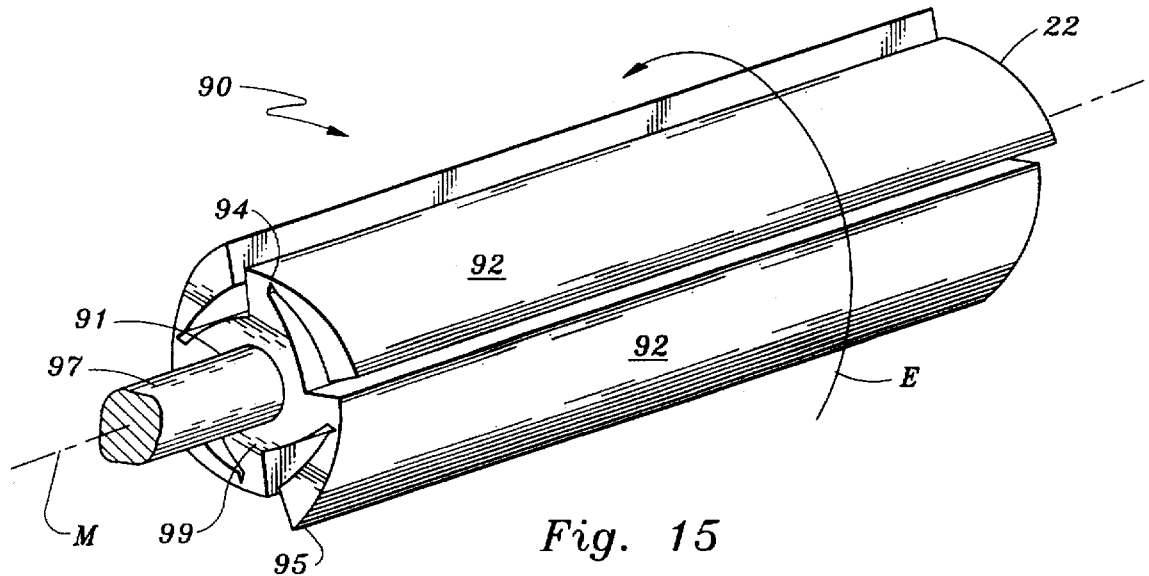
FIG. 15 is a perspective view of the rotor of this invention.
Figure 16:
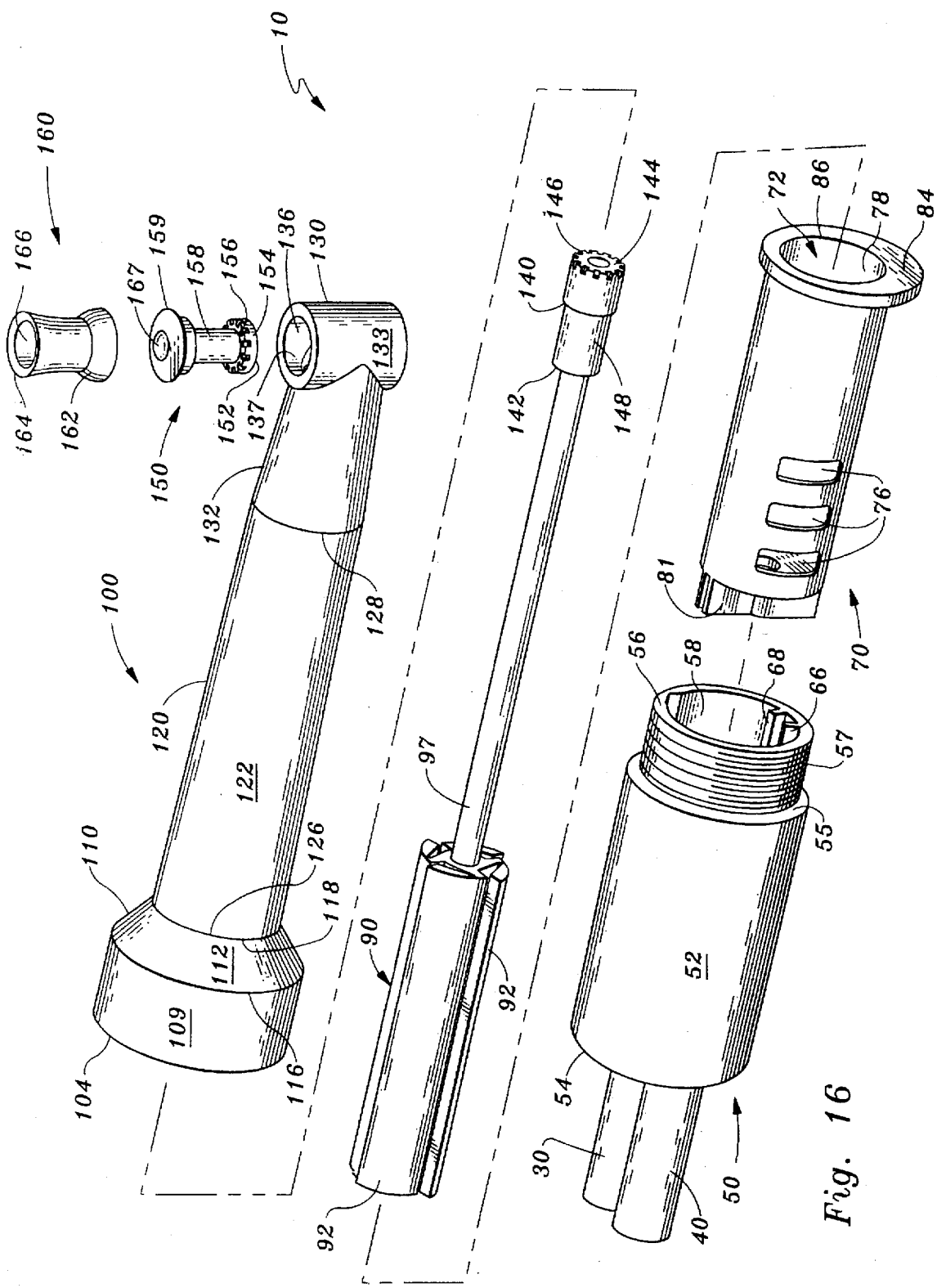
FIG. 16 is a perspective exploded parts view of this invention with individual parts separated according to an order of assembly.

The rotor 90 is rotatably supported within the cylinder 72 of the insert 70. The cylinder 72 provides a cavity for supporting the rotor 90 within the handpiece 10. The rotor 90 includes a plurality vanes 92 pivotably supported by the rotor 90 so that the vanes 92 can pivot between a first position adjacent the rotor 90 to a second position pivoted away from the rotor 90. The rotor 90 is oriented with a rotational axis M (FIGS. 13 and 15) offset from a central axis N of the cylinder 72 (FIG. 9). This offset between the axis M and the axis N allows the vanes 92 to pivot between the first position and the second position as the rotor 90 rotates about arrow E.

High pressure fluid passing through the entrance 30 along arrow A has access to the high pressure chamber 80 and the inlet ports 74. When the high pressure fluid enters the cylinder 72 through the inlet ports 74, the rotor 90 is caused to rotate about arrow E. Rotor 90 rotation in turn causes the output shaft 97 to rotate. The high pressure fluid is simultaneously decreased in pressure, passed through the exhaust ports 76 and the low pressure chamber 82 and then exhausted out of the outlet 40 along arrow D. The output shaft is coupled to a long gear 140 which interfaces with a short gear 150 perpendicular thereto. The short gear 150 is releasably coupled to the prophylaxis cup 160. A cap 100 attaches to an output end 56 of the housing 50 opposite the rear end 54 supporting the entrance 30 and the outlet 40. The cap holds the insert 70 and rotor 90 within the housing 50 and includes a sleeve 120 for surrounding the output shaft 97. The sleeve 120 supports a head 130 which rotatably supports the short gear 150.

More specifically, and with reference to FIGS. 1 through 4 and 10 through 12, details of the entrance 30 and outlet 40 are described. The entrance 30 is preferably a hollow cylindrical conduit which extends a short distance perpendicularly away from the rear end 54 of the housing 50. The entrance 30 includes an exterior 32 which is substantially cylindrical and an interior 36 which is substantially cylindrical. The entrance 30 extends from a tip 34 spaced from the rear end 54 of the housing 50 to a root 38 adjacent the rear end 54 of the housing 50.

An interior of the housing 50 includes an access wall 60 substantially parallel to and spaced from the rear end 54 of the housing 50. An influx vent 62 passes through the access wall 60 and rear end 54 at a location adjacent the root 38 of the entrance 30.

The root 38 includes an entrance hole 39 adjacent the interior 36 of the entrance 30. The entrance hole 39 is directly adjacent the influx vent 62 and provides access between the interior 36 of the entrance 30 and the interior of the housing 50.

The outlet 40 is a hollow cylindrical construct extending substantially perpendicularly from the rear end 54 of the housing 50. The outlet 40 includes a cylindrical outer surface 42 concentric with a cylindrical inner surface 46. The outlet 40 extends from an end 44 distant from the rear end 54 to a base 48 adjacent the rear end 54.

An outlet hole 49 defines a portion of the inner surface 46 closest to the base 48 of the outlet 40. The outlet hole 49 is directly adjacent a return vent 64 passing through the access wall 60 adjacent to the influx vent 62. Preferably, the inner surface 46 and outer surface 42 of the outlet 40 are greater in diameter than the interior 36 and exterior 32 of the entrance 30. This dimensional dissimilarity assists in minimizing back pressure in the outlet 40, thereby enhancing performance of the handpiece 10.

Preferably, a stop 45 extends between the entrance 30 and the outlet 40 connecting the exterior 32 to the outer surface 42. The stop 45 provides an indication to a user as to when a high pressure fluid hose placed over the entrance 30 or outlet 40 has been sufficiently slid over the entrance 30 or outlet 40 to mate the hose to the entrance 30 or output 40. The entrance 30 can be coupled to any source of fluid including compressible and incompressible fluid, high pressure and low pressure fluid, and high and low velocity fluid. Preferably, however, the entrance 30 is coupled to an air compressor such that compressed air is supplied through the entrance 30 and into the handpiece 10. The outlet 40 can either be left open to discharge compressed air into the surrounding environment or can have a conduit connected thereto to direct air passing out of the handpiece 10 to a distant location. Alternatively, the outlet 40 can be coupled to a source of vacuum to pull fluid through the device. Alternatively, a combination of both elevated pressure fluid and vacuum could be utilized to provide a "push-pull" system. Preferably, the entrance 30 and outlet 40 are integrally formed with the housing 50. Alternatively, the entrance 30 and outlet 40 can be connected to the housing 50 through use of an adhesive or other fastening means.

With respect to FIGS. 1 through 6 and 10 through 12, details of the housing 50 are described. The housing 50 is essentially a hollow substantially cylindrical construct having an outer cylindrical wall 52 and an inner cylindrical wall 58. The housing 50 extends from the rear end 54 to an output end 56. Adjacent the output end 56, the housing 50 includes a step 55 at which the outer cylindrical wall 52 steps down to a decreased diameter and threads 57 extending between the step 55 and the output end 56. The threads 57 are configured to threadably receive the cap 100 thereon. The inner cylindrical wall 58 extends from the output end 56 to the access wall 60 while maintaining a substantially circular cross section. The access wall 60 includes the influx vent 62 and return vent 64 passing therethrough at locations corresponding with the entrance hole 39 and the outlet hole 49, respectively.

The inner cylindrical wall 58 includes a notch 65 at a portion thereof adjacent to where the exhaust ports 76 of the insert 70 are located. This notch 65 provides excess cross sectional area for fluid to pass out of the cylinder 72, to discourage any back pressure from building up during operation of the handpiece 10. The notch 65 increases a radius of the inner cylindrical wall 58 slightly for approximately a tenth of the inner cylindrical wall 58. Preferably, the notch 65 extends from the rear end 54 to the output end 56 of the inner cylindrical wall 58, for ease in forming the notch 65. Alternatively, the notch 65 can be provided only adjacent the specific locations of the exhaust ports 76.

A first divider wall 66 and second divider wall 68 are provided extending from the inner cylindrical wall 58 toward a geometric center of the housing 50 from the access wall 60 to the output end 56 of the housing 50. The first divider wall 66 and second divider wall 68 preferably extend to a height similar to a difference between a diameter of the inner cylindrical wall 58 of the housing 50 and a diameter of the insert 70. Thus, the divider walls 66, 68 support the insert 70 tightly within the housing 50 while providing the high pressure chamber 80 adjacent the second divider wall 68 and the low pressure chamber 82 adjacent the first divider wall 66.

The divider walls 66, 68 prevent fluid from passing between the high pressure chamber 80 and the low pressure chamber 82. A locator tab 69 is oriented at a junction between the inner cylindrical wall 58 and the access wall 60 at a location rotated approximately 180° away from the divider walls 66, 68. The locator tab 69 extends only slightly away from the access wall 60 and assists in appropriately orienting the insert 70 rotationally within the housing 50 when positioned within a slot 61 in the insert 70.

As shown in FIG. 5, the inner cylindrical wall 58 can be slightly recessed at a crescent indentation 67 thereof opposite the divider wall 66, 68 to further encourage the insert 70 to be securely held within the housing 50. The crescent indentation 67 has a radius of curvature matching a radius of curvature of the insert 70 and causes a thickness of the housing 50 between the outer cylindrical wall 52 and the inner cylindrical wall 58 to be slightly reduced. Alternatively, as shown in FIG. 12, the inner cylindrical wall 58 can be substantially circular in cross section.

With reference now to FIGS. 2 through 9, details of the insert 70 are described. The insert 70 is preferably a substantially cylindrical hollow construct dimensioned to nest within the interior of the housing 50. The insert 70 includes a cylinder 72 on an interior thereof which is substantially circular in cross section. The insert 70 extends from an end wall 88 configured to be oriented adjacent the access wall 60 of the housing 50 and an open end 86 opposite the end wall 88. The open end 86 includes an annulus 84 thereon which extends radially away from the open end 86 in a plane substantially perpendicular to the central axis N of the cylinder 72. The annulus has a lobe 73 at a lower portion thereof which conforms to a form of the housing 50 at the output end 56. This lobe 73 thus covers ends of the dividers 66, 68. The cylinder 72 within the insert 70 is defined by a cylindrical wall 78 extending from the end wall 88 to the open end 86.

A plurality of inlet ports 74 pass through the insert 70 and into the cylinder 72. The inlet ports 74 are oriented on a side of the insert 70 such that they provide fluid communication between the cylinder 72 and the high pressure chamber 80 within the housing 50. This high pressure chamber 80 is further placed in fluid communication with the influx vent 62 and the access wall 60 so that elevated pressure pneumatic fluid passing through the entrance 30 has fluid access into the cylinder 72 through the inlet ports 74. Preferably, the inlet ports 74 are provided along a line substantially parallel to the central axis N of the cylinder 72. The inlet ports 74 can be located at a variety of different locations between the open end 86 and the end wall 88. Preferably, the inlet ports 74 are located substantially at a mid-point between the open end 86 and the end wall 88.

A plurality of exhaust ports 76 pass through the insert 70 and into the cylinder 72 on a side of the insert 70 opposite that of the inlet ports 74. The exhaust ports 76 are located such that when the insert 70 is located within the housing 50, the exhaust ports 76 are in fluid communication with the low pressure chamber 82. The low pressure chamber 82 is oriented to be in fluid communication with the outlet 40 so that pneumatic fluid exiting the cylinder 72 through the exhaust port 76 can be drawn out of the housing 50 through the outlet 40. Preferably, the exhaust ports 76 are provided along a line substantially parallel to the central axis N and at a mid-point between the end wall 88 and the open end 86.

With reference to FIG. 5, sizes and positions of the inlet ports 74 and exhaust ports 76 are described in detail. Initially, note the location of a seal point SP at a substantially bottom dead center portion of the cylinder 72. The inlet ports 74 begin approximately 15° counterclockwise (FIG. 5) from the seal point SP. The inlet ports 74 preferably extend for approximately 30°. The exhaust ports 76 preferably stop at a location 60° away from the seal point SP. The inlet ports 74 end and the exhaust ports 76 begin with preferably approximately 180° therebetween. While these inlet ports 74 and exhaust ports 76 configurations have been identified as preferred, various different sizes of inlet ports 74 and exhaust ports 76 in various different relative locations of ports 74, 76 can be effectively utilized.

The inlet port 74 and exhaust port 76 are spaced sufficiently apart on a side of the rotor 90 opposite the seal point SP to insure that the inlet port 74 and exhaust port 76 are never in direct fluid communication with each other. This characteristic can be obtained by locating the inlet ports 74 and outlet ports 76 angularly spaced apart by a distance not less than 360° divided by the number of vanes 92. This ensures that the inlet ports 74 and outlet ports 76 are never in direct communication without a vane 92 therebetween. Preferably, as soon as a tip 95 of a vane 92 passes an end of the inlet port 74, a tip 95 of a preceding vane 92 is just passing a beginning of the exhaust port 76. In this way, compression and expansion of the pneumatic fluid is minimized and thermodynamic heating and cooling effects are minimized within the cylinder 72. Preferably, the inlet ports 74 begin sufficiently close to the seal point SP to prevent a substantial amount of vacuum being formed behind the vanes 92 as the vanes 92 rotate counterclockwise (FIG. 5) away from the seal point SP.

The end wall 88 of the insert 70 includes an end wall divider 81 oriented thereon and extending toward the access wall 60. The end wall divider 81 includes a first leg 83 oriented to be positioned adjacent the first divider wall 66 and a second leg 85 oriented to be adjacent the second divider wall 68. The slot 61 is formed in the end wall divider 81 adjacent the locator tab 69. The slot 61 receives the locator tab 69 therein to prevent the insert 70 from rotating within the housing 50. The end wall divider 81 contacts the access wall 60. Thus, the divider 81 prevents pneumatic fluid from passing around the end wall 88 of the insert 70 between the high pressure chamber 80 and the low pressure chamber 82.

The cylinder 72 includes a bearing 89 at a portion thereof adjacent the end wall 88. The bearing 89 is a substantially cylindrical recess having a geometric center slightly spaced from the central axis N of the insert 70. Preferably, the bearing 89 is located such that when the insert 70 is oriented within the housing 50, the bearing 89 has a geometric center thereof oriented along a geometric center line of the housing 50. The bearing 89 assists in supporting the rotor 90 within the cylinder 72 as described below.

With reference now to FIGS. 2 through 5 and 13 through 15, details of the rotor 90 are described. The rotor 90 is sized to nest within the cylinder 72 of the insert 70 and includes a substantially rigid trunk 24 and a plurality of vanes 92 pivotably attached to the trunk 24 of the rotor 90. The rotor 90 preferably has a hollow core 91 passing between a hub end 22 of the rotor 90 and an output end 99 of the rotor 90. The core 91 can receive an output shaft 97 passing entirely therethrough such that the output shaft 97 forms a hub 20 extending slightly from the hub end 22 of the rotor 90 and extends out of the output end 99 for coupling to the prophylaxis cup 160.

Preferably, the output shaft 97 is formed from a material exhibiting more rigidity than a material forming the trunk 24 and vanes 92 of the rotor 90. The output shaft 97 thus acts as a backbone, preventing the rotor 90 from bending between the hub end 22 and the output end 99. For instance, the trunk 24 and vanes 92 can be formed of a plastic such as a polymeric hydrocarbon while the output shaft 97 can be formed of steel. Alternatively, the shaft 97 is integrally formed from the same material as the trunk 24 and vanes 92.

The trunk 24 surrounds the core 91 and includes a plurality of posts 93 extending away from the trunk 24. The posts 93 preferably extend along lines substantially tangent to the core 91 of the rotor 90. Each post 93 includes a hinge 94 on a trailing portion of an end thereof distant from the trunk 24 which supports a vane 92 thereon. A recess 26 is provided between each post 93 which is preferably shaped to allow one of the vanes 92 to be received within an adjacent recess 26 when sufficient force is applied to the vanes 92 to cause the vanes 92 to pivot about the hinge 94.

The vanes 92 include a forward surface 96 which is arcuate with a radius of curvature similar to a radius of the rotor 90 between the rotational axis M of the rotor 90 and the ends of the posts 93 most distant from the core 91. The recesses 26 are sufficiently deep to allow the vanes 92 to pivot down entirely within the recesses 26 such that no portion of the vanes 92 extend beyond the posts 93 when a rearward surface 98 of each vane 92 opposite the forward surface 96 is adjacent the trunk 24 within the recess 26. When all of the vanes 92 are retracted into the recess 26 of the rotor 90, the rotor 90 exhibits a substantially circular cross-section.

Each vane 92 has a first position entirely within the recess 26 and a second position pivoted out of the recess 26 along arrow F an amount necessary to keep a tip 95 of the vane 92 distant from the hinge 94 in contact with the cylindrical wall 78. The cylinder 72 preferably has a diameter less than a diameter of a circle scribed by the tips 95 of the vanes 92 when the vanes 92 are in the second position, such that the vanes 92 can maintain contact with the cylindrical wall 78.

The hinges 94 are preferably biased such that the vanes 92 are encouraged to extend out of the recesses 26 when no forces are applied forcing the vanes 92 into the recesses 26. This biasing is preferably programmed into the rotor 90 when the rotor 90 is formed. One method of forming the rotor 90 is through injection molding of an organic polymeric material where the vanes 92 and trunk 24 are formed simultaneously as a single unit within an injection mold. The hinge 94 is formed by providing a sufficiently thin portion of the mold to allow bending of the material forming the rotor 90. This method of manufacture greatly reduces a cost and complexity of the handpiece 10, making it more economical for dental practitioners to dispose of the handpiece 10 after a single use. A possibility of disease transmission is thus further diminished.

The mold is shaped so that the natural position of the vanes 92 is extended out of the recess 26, but is shaped to provide the recesses 26 with a size and shape which allows the vanes 92 to be pivoted into an adjacent recess 26 without extending beyond the posts 93. In this way, each vane 92 is effectively "spring loaded" (i.e., programmed with a memory) to attempt to retract out of the recess 26 at all times. The vanes 92 are preferably formed with a static position similar to the second position. This biasing of the vanes 92 toward the second position helps ensure that the vanes 92 maintain contact with the cylindrical wall 78, especially during start up when no centrifugal force is acting upon the vanes 92. While biasing the vanes 92 is preferred, the rotor 90 can also self-start without biasing.

Figure 14:
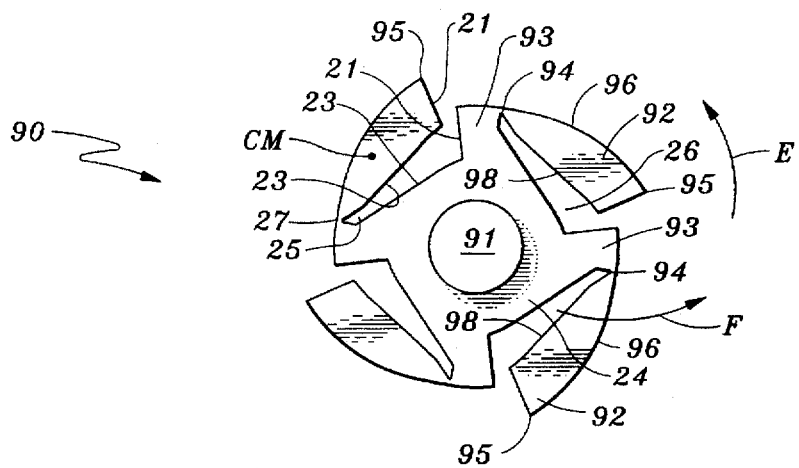
FIG. 14 is a front view of a portion of that which is shown in FIG. 13.

With particular reference to FIG. 14, the rotor 90 can be identified as a radially symmetrical constant cross-section construct. Viewed in section, the rotor 90 preferably includes four identical regions, with each region including one vane 92. However, additional regions can be included. The rotor 90 is circular in cross-section when the vanes 92 are collapsed against the trunk 24. Each vane 92 can be alternatively formed by a radial cut 21, extending from the tip 95 partially toward the core 91, followed by a secant cut 23. The secant cut 23 extends from an inner end of the radial cut 21 to a location just short of a surface 27 of the material, such that remaining material between the secant cut 23 and the surface 27 can be flexed providing the hinge 94. The secant cut 23 adjacent the hinge 94 is slightly widened to form a hinge relief region 25. This region 25 assists in allowing the vane 92 to flex totally into the recess 26 and present a circular surface 27 to the seal point SP (FIG. 4), which maintains contact with the cylindrical wall 78 regardless of the rotational orientation of the rotor 90.

Each vane 92 has a center of mass CM which affects a force with which the vanes 92 address the cylindrical wall 78. The location of the center of mass CM can be adjusted as desired to change a free speed of the rotor 90. For instance, the vanes 92 can be modified in geometry or weights such as higher density material can be added to portions of the vanes 92 during manufacture. Adjusting a location of the center of mass CM also alters a flywheel effect of the rotor 90. With the center of mass CM more distant from the hinge 94, a moment of inertia of the rotor 90 is altered. Also, adding or subtracting weight from the vanes 92 alters the inertia of the rotor 90. The vanes 92 contact with the cylindrical wall 78 acting as a governor for the free speed of the rotor 90. By altering the mass and center of mass CM of the vanes 92, a speed at which the rotor 90 is governed can be altered as desired.

The hub 20 is sized to be rotatably supported within the bearing 89 of the cylinder 72. The bearing 89 and hub 20 thus interact in a journal bearing fashion to support the hub end 22 of the rotor 90. The output end 99 of the rotor 90 is supported by an opening 108 (FIG. 4) formed in the cap 100 which receives the output shaft 97. The opening 108 and bearing 89 are positioned to cause the rotor 90 to have its rotational axis M offset from the central axis N of the cylinder 72. This offset is preferably sufficient to cause the rotor 90 to always contact the cylindrical wall 78 of the cylinder 72 at the seal point SP between the inlet ports 74 and the exhaust ports 76. Thus, a distance between the rotational axis M of the rotor 90 and the central axis N of the cylinder 72 is equal to a radius of the cylinder 72 minus a radius that the posts 93 extend from the rotational axis M. This offset of the axes M, N causes the vanes 92 to, in essence, orbit a geometric center of the trunk 24 as the rotor 90 turns such that the vanes 92 have a perigee adjacent the seal point SP and an apogee opposite the seal point SP and between the ports 74, 76.

The cap 100, shown in FIGS. 1, 2, 4 and 16, threads onto the threads 57 of the housing 50 with cap threads 103 until a bearing wall 105 comes into contact with the annulus 84 of the open end 86. The cap 100 includes bearing surface 106 supporting the output end 99 of the rotor 90 and having the opening 108 located at a center thereof and in alignment with the output shaft 97 when the rotor 90 and insert 70 are oriented within the housing 50. The cap 100 is preferably formed so that when it is entirely threaded upon the threads 57 of the housing 50, fluid flow between the high pressure chamber 80 and low pressure chamber 82 is prevented adjacent the cap 100 and the substantially planar bearing surface 106 is provided for bearing of the output end 99 of the rotor 90 thereagainst. The cap 100 thus holds the insert 70 and rotor 90 within the housing 50. A bearing wall 105 supports the bearing surface 106 and an opposite surface 107 parallel to and spaced from the bearing surface 106.

The cap 100 extends from the attached end 104 adjacent the housing 50 to the prophylaxis end 128 spaced from the housing 50. The cap 100 includes a cylindrical portion 109 adjacent the attached end 104, a frustum 110 on a side of the cylindrical portion 109 spaced from the attached end 104 and the sleeve 120 extending from the frustum 110 to the prophylaxis end 128 of the cap 100. The frustum 110 has an outer surface 112 which extends from a large diameter end 116 adjacent the cylindrical portion 109 and a small diameter end 118 opposite the large diameter end 116. An inner surface 114 is substantially parallel to and inboard with respect to the outer surface 112. The inner surface 114 forms part of an interior region of the cap 100 which surrounds the output shaft 97 to prevent objects from coming into contact with the rotating output shaft 97.

The sleeve 120 includes an exterior surface 122 spaced from an interior surface 124. The exterior surface 122 preferably slightly tapers from the frustum 110 to the prophylaxis end 128. In addition, the exterior surface 122 can support ribs or other friction enhancing means to assist a dental practitioner in grasping the sleeve 120, especially when using surgical gloves. The interior surface 124 assists in protecting the output shaft 97 in a manner similar to the inner surface 114 of the frustum 110.

The sleeve 120 supports a head 130 most distant from the housing 50. A neck 132 is interposed between the prophylaxis end 128 of the sleeve 120 and the head 130. The head 130 includes an outer surface 133 on an exterior thereof and a gear chamber 135 on an interior thereof. The gear chamber 135 is spaced from the interior surface 124 of the sleeve 120 by a gear support 134. The gear support 134 is sized to receive the long gear 140 therethrough and support the long gear 140 without allowing the long gear 140 to be translated radially. The gear chamber 135 includes an output opening 136 at one end thereof and a back wall 138 opposite the output opening 136. A cylindrical sidewall 137 is interposed between the output opening 136 and back wall 138. The output opening 136, back wall 138 and cylindrical sidewall 137 are dimensioned to support the short gear 150 therein.

The long gear 140 includes an attached end 142 which is coupled to the output shaft 97. The long gear 140 has a face 144 opposite the attached end 142 with a sidewall 148 interposed between the attached end 142 and the face 144. Preferably, the side wall 148 is substantially cylindrical and steps up to a larger diameter adjacent the face 144. A plurality of teeth 146 are provided along a periphery of the face 144. The gear support 134 is dimensioned to support the long gear 140 along a portion of the long gear 140 closer to the face 144 than to the attached end 142 but with the face 144 extending beyond the gear support 134 and into the gear chamber 135. Thus, the teeth 146 are presented within the gear chamber 135 to interact with the short gear 150.

The short gear 150 includes a back end 152 at one end thereof and an annular bearing 159 at an opposite end thereof. A shaft 158 is interposed between the back end 152 and the annular bearing 159. Preferably, the shaft 158 is substantially cylindrical. The back end 152 includes a lip 154 which is defined by a region having a slightly larger diameter than the shaft 158. The lip 154 includes a plurality of teeth 156 on a side thereof opposite the back end 152. The teeth 156 are oriented, sized and shaped to interact with the teeth 146 of the long gear 140. By positioning the teeth 156 on a side of the lip 154 opposite the back end 152, the short gear 150 is retained in place within the gear chamber 135 by the face 144 of the long gear 140.

The annular bearing 159 has a diameter slightly greater than the output opening 136 of the head 130. Thus, the annular bearing 159 prevents the short gear 150 from extending into the gear chamber 135 a distance which would cause the teeth 156 to fall out of engagement with the teeth 146 of the long gear 140. The annular bearing 159 includes a connector knob 167 on a surface thereof opposite the shaft 158 of the short gear 150. The connector knob 167 is configured to attach to the prophylaxis cup 160. Alternatively, a threaded shaft or threaded bore can be provided for interfacing with a complementally formed threaded shaft or threaded bore of the prophylaxis cup 160. The connector knob 167 allows the prophylaxis cup 160 to be detached from the connector knob 167 and short gear 150 if replacement of the prophylaxis cup 160 is desired.

The prophylaxis cup 160 is preferably formed from a resilient rubber material and includes a base 162 at an end thereof which connects to the connector knob 167 and a rim 164 spaced from the base 162. An interior 166 is surrounded by the rim 164 and provides a region within which polishing paste can be located for providing a desired abrasiveness during dental prophylaxis.

Figure 4:
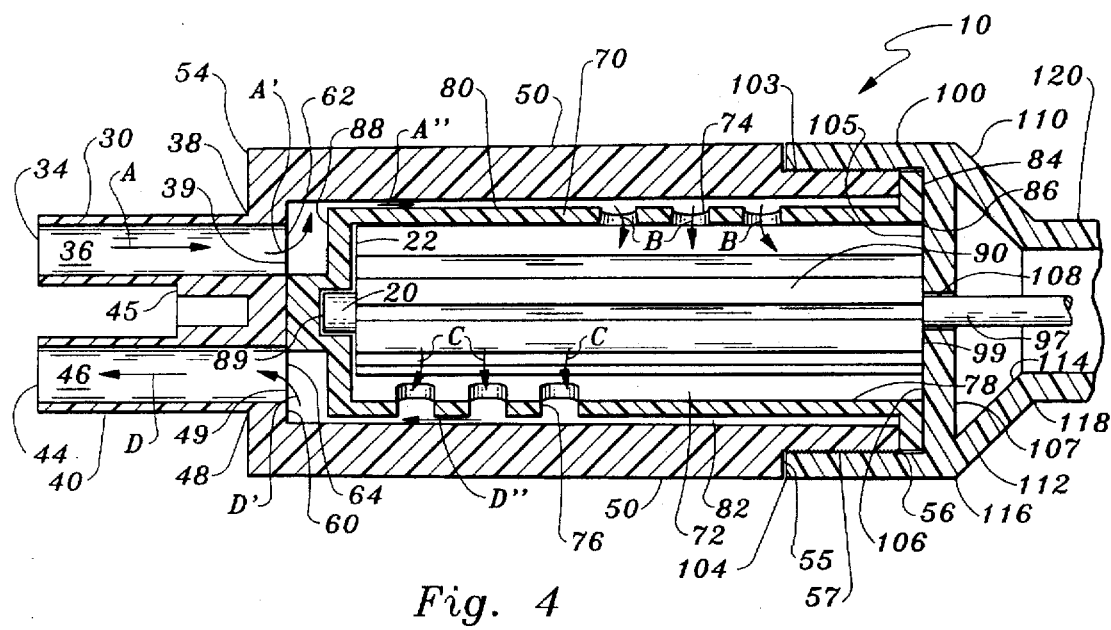
FIG. 4 is a sectional view taken along line 4—4 of FIG. 3.

In use and operation, and with reference to FIGS. 3 through 5, details of the operation of the handpiece 10 are described in detail. Initially, preferably high pressure fluid, such as air, is passed into the entrance 30 along arrow A. The fluid can alternatively be incompressible fluid having a high or low pressure or velocity. The fluid then passes through the entrance hole 39 and influx vent 62 along arrow A' and through the high pressure chamber 80 along arrow A". If low pressure fluid is utilized at high velocity, this fluid would also pass through the chamber 80. The high pressure fluid then enters the cylinder 72 through the inlet ports 74 along arrow B. The fluid passes around the rotor 90 along arrow B', causing the rotor 90 to turn about arrow E.

The rotor 90 is primarily caused to rotate due to a combination of the pressure difference between the high pressure chamber 80 and the low pressure chamber 82 and the offset of the rotor 90 within the cylinder 72. Other factors contributing to rotor 90 rotation can include a velocity of the fluid addressing the vane 92 of the rotor 90 and the ability of the fluid to expand within the cylinder 72. These other factors vary in importance from negligible to substantial depending on the specific configuration of the handpiece 10 and the nature of the fluid utilized by the handpiece 10. In general, incompressible fluids could provide high pressure, high velocity or both to cause rotor 90 rotation. Torque exhibited by the rotor is maximized by allowing the total surfaces of the vanes 92 to be exposed to the drive fluid rather than just portions thereof as exhibited by prior art sliding vane rotors.

As the rotor 90 rotates along arrow E, the vanes 92 are caused to pivot about the hinge 94 along arrow F. This pivoting is caused by a combination of the biasing built into the hinge 94, centrifugal forces and fluid pressure tending to cause the vanes 92 to extend away from the rotational axis M (FIGS. 13 and 15) of the rotor 90. In fact, if forces resist rotor 90 rotation, the vanes 92 are still caused to pivot along arrow F due to the fluid pressure and torque is exhibited by the rotor 90. The high pressure fluid then comes into contact with the exhaust port 76 where a pressure of the high pressure fluid is decreased. The fluid passes through the exhaust port 76 along arrow C and into the low pressure chamber 82. The fluid then passes along arrow D" through the low pressure chamber 82 to the return vent 64 and outlet hole 49 along arrow D' and then out of the outlet 40 along arrow D. If low pressure fluid is utilized, the chamber 82 would support reduced velocity fluid. Rotation of the rotor 90 causes the output shaft 97 coupled thereto to rotate about arrow E (FIG. 1). Each vane 92 preferably passes the outlet ports 76, the seal point SP and then the inlet ports 74, in sequence. This rotation in turn causes the long gear 140, short gear 150 and prophylaxis cup 160 to rotate.

The tips 95 of the vanes 92 preferably remain in contact with the cylindrical wall 78 of the cylinder 72 most of the time. This dragging of the tips 95 of the vanes 92 against the cylindrical wall 78 creates frictional forces which inhibit the rotor 90 from exceeding certain speeds. As the rotor 90 rotates faster and faster, a centrifugal force of the vanes 92 away from the rotor 90 increases, increasing a force that the vanes 92 exert normal to the cylindrical wall 78. In addition, pressure of the fluid against the vanes 92 increases a radially outward force against the cavity wall. This in turn increases a frictional force opposing rotation of the rotor 90, thus limiting speed. Because the vanes 92 pivot into contact with the wall 78, precise tolerances for the vane 92 dimensions need not be maintained during manufacture to provide an appropriate seal between the tips 95 and the wall 78.

Hence, the handpiece 10 is provided with a maximum free speed at which frictional forces generated between the tips 95 of the vanes 92 of the rotor 90 are equal to rotational forces imparted against the vanes 92 of the rotor 90 by the differential pressure between the high pressure chamber 80 and the low pressure chamber 82. As long as a pressure differential exists between the high pressure chamber 80 and low pressure chamber 82, the seal point SP is maintained so that fluid cannot pass from the inlet ports 74 to the exhaust port 76 through the seal point SP. With the vanes 92 remaining in contact with the cylindrical wall 78, a torque is applied about the rotational axis M of the rotor 90, encouraging the rotor 90 to rotate with or without actual rotor 90 rotation. The cylinder 72 and rotor 90 are configured such that a volume between adjacent vanes 92 and a pressure of fluid between the inlet ports 74 and exhaust ports 76 both remain substantially constant. Thus, an adiabatic expansion of the fluid is kept to a minimum. This feature minimizes any thermal effect on the fluid or the device 10, which could otherwise damage the device 10.

Figure 4A:
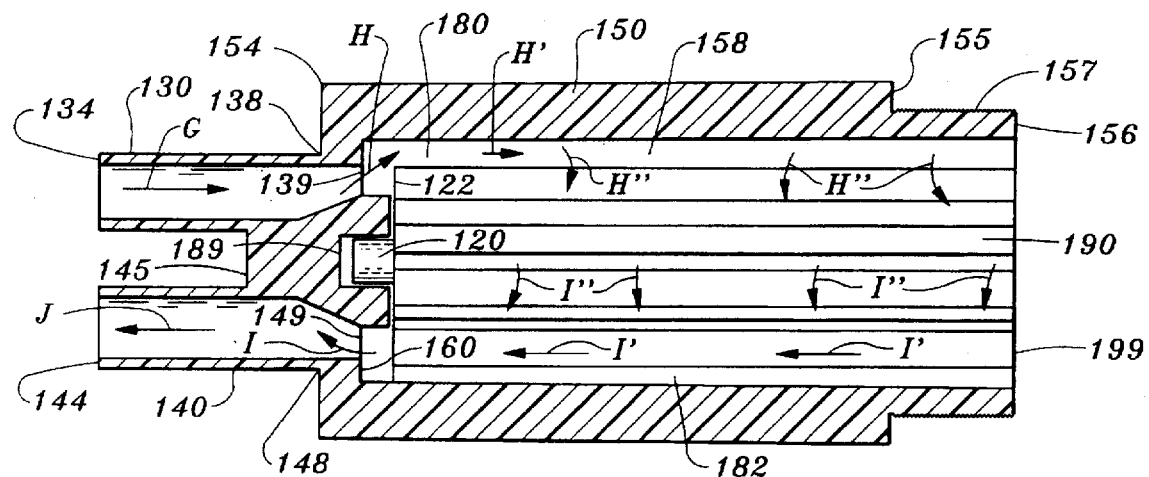
FIG. 4A is an alternative embodiment of that which is shown in FIG. 4.
Figure 5A:
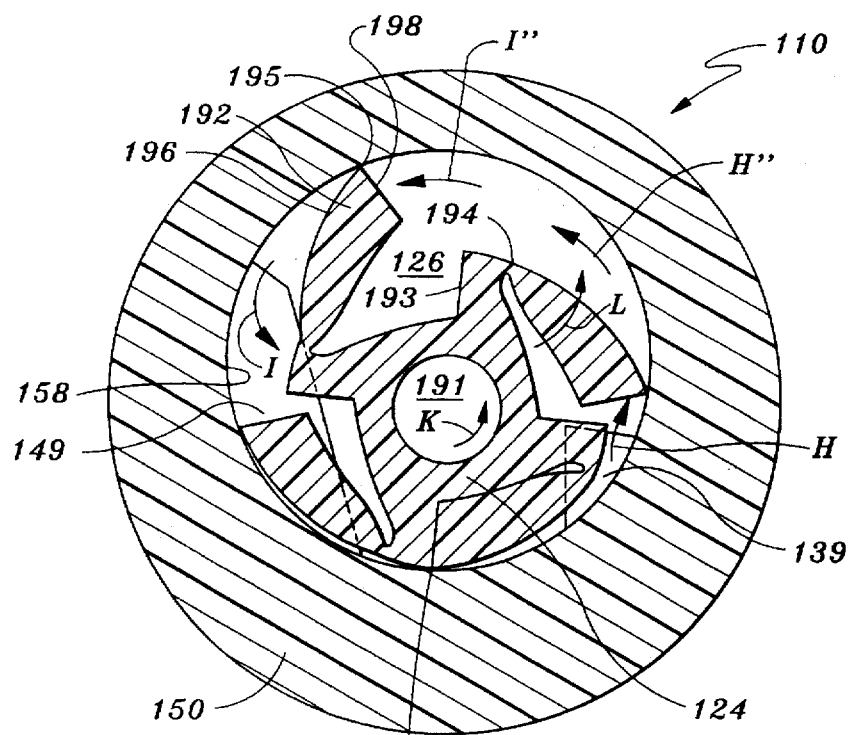
FIG. 5A is an alternative embodiment of that which is shown in FIG. 5.

With reference now to FIGS. 4A and 5A, details of an alternative embodiment of the handpiece 10 are described. In this alternative embodiment, a handpiece 110 is provided which incorporates essential features of the insert 70 of the preferred embodiment directly into the housing 50 of the preferred embodiment. Hence, a housing 150 is provided having a rear end 154 and an output end 156 with a step 155 therebetween and threads 157 between the step 155 and the output end 156. The housing 150 includes an inner cylindrical wall 158 which provides a cylinder within which a rotor 190 is supported.

The housing 150 includes an access wall 160 which directly supports a bearing 189 thereon to provide rotational support for a hub 120 of the rotor 190. The inlet ports 74 and exhaust ports 76 of the preferred embodiment are replaced with an entrance hole 139 and an outlet hole 149. A stop 145 is interposed between the entrance 130 and outlet 140 to define a depth to which hoses can overlie the entrance 130 and outlet 140. The entrance 130 extends from a tip 134 to a root 138. The outlet 40 extends from an end 144 to a base 148. The inlet hole 139 is interposed between an entrance 130 and a high pressure chamber 180 of the housing 150. The outlet hole 149 is interposed between an outlet 140 and a low pressure chamber 182 oriented within the housing 150.

Preferably, the inlet hole 139 is positioned to minimize a thrust placed on the rotor 190 in a direction away from the entrance 130. This helps minimize any leakage of air around the rotor 190 adjacent the access wall 160. The high pressure chamber 180 and low pressure chamber 182 are spaced apart by the seal point SP and points of contact between the tips 195 of the vanes 192 of the rotor 190 and the inner cylindrical wall 158 of the housing 150.

The rotor 190 extends from a hub end 122 to an output end 199. The hub 120 extends through a core 191 of the rotor 190 and is supported within the bearing 189 of the housing 150. The rotor 190 includes a plurality of posts 193 extending away from a trunk 124 of the rotor 190. Each post 193 supports a hinge 194 thereon which in turn is connected to one of the vanes 192. Each vane 192 includes a forward surface 196 and a rearward surface 198 similar to the surfaces 96, 98 of the rotor 90 of the preferred embodiment.

In use and operation, the handpiece 110 operates in the following manner. Initially, elevated pressure pneumatic fluid passes through the entrance 30 along arrow G. The fluid then passes from the entrance 30 through the entrance hole 139 along arrow H and into the high pressure chamber 180 along arrow H'. The high pressure fluid then rotates around the rotor 190 along arrow H", past a location 180° opposed from the seal point SP along arrow 1" and into fluid contact with the low pressure chamber 182 where the fluid is decreased in pressure and migrates along arrow I'. The fluid then passes through the outlet hole 149 along arrow I and then into the outlet 140 along arrow J.

As the fluid passes over the rotor 190, the rotor 190 is caused to rotate about arrow K. Also, the vanes 192 are caused to pivot about the hinge 194 along arrow L and out of recesses 126. The entrance hole 139 and outlet hole 149 are configured such that fluid is prevented from being in direct contact between the high pressure chamber 180 and the low pressure chamber 182 without rotation of the rotor 190.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A hand held disposable dental prophylaxis handpiece driven by a source of elevated pressure, compressible fluid, comprising in combination:

an elongated plastic housing dimensioned to be supported in one's hand much like a pen;

a plastic fluid reaction device receiving the fluid as input and having a rotating shaft as an output, said fluid reaction device including a plastic rotor having a substantially rigid plastic trunk integrally formed therewith, a plurality of plastic vanes integrally formed therewith, and a means to pivotably attach said vanes to said trunk, a hollow cavity, said cavity including means to inlet fluid into said cavity, means to exhaust fluid out of said cavity, and means to rotatably support said trunk of said rotor within said cavity wherein said pivotable attachment means includes plastic hinges each integrally formed with and interposed between each said vane and said trunk, said hinge including means to apply a force causing said vane to be urged towards and contact a periphery of said hollow cavity;

a prophylaxis cup;

coupling means from said cup to said rotating shaft such that rotation of said shaft rotates said prophylaxis cup;

said rotating shaft output coupled to said rotor such that when fluid enters said cavity, said shaft is caused to rotate, and each said vane having an integrally formed portion which is larger away from the hinge than adjacent the hinge so as to act as a governor and a flywheel, whereby the elevated pressure compressible fluid driving said vanes can be controlled to provide substantially constant speed and high torque.

2. The handpiece of claim 1 wherein said means to rotatably support said rotor within said cavity includes a means to support said rotor with a rotational axis of said rotor spaced from a central axis of said hollow cavity.

3. The handpiece of claim 2 wherein a seal point is provided between said rotor and said cavity, said seal point located between said inlet means and said exhaust means, said seal point defined by at least one portion of said rotor contacting said cavity between said inlet means and said exhaust means;

whereby fluid passing through said inlet means and into said cavity is prevented from accessing said exhaust means by passing around a side of said rotor closest to said seal point.

4. The handpiece of claim 3 wherein said rotor includes a recess adjacent each vane, each said recess having a contour which can receive an adjacent said vane therein when said vane is pivoted about said pivotable attachment means.

5. A disposable dental prophylaxis handpiece driven by a source of elevated pressure, compressible fluid, comprising in combination:

a housing;

a fluid reaction device receiving fluid as input and having a rotating shaft as an output, the fluid reaction device including a rotor having a substantially rigid trunk, a plurality of vanes, and a means to pivotably attach said vanes to said trunk, a hollow cavity, said cavity including means to inlet fluid into said cavity, means to exhaust fluid out of said cavity, and means to rotatably support said trunk of said rotor within said cavity;

a prophylaxis cup;

coupling means from said cup to said rotating shaft such that rotation of said shaft rotates said prophylaxis cup;

said rotating shaft output coupled to said rotor such that when fluid enters said cavity, said shaft is caused to rotate;

wherein said means to rotatably support said rotor within said cavity includes a means to support said rotor with a rotational axis of said rotor spaced from a central axis of said hollow cavity;

wherein a seal point is provided between said rotor and said cavity, said seal point located between said inlet means and said exhaust means, said seal point defined by at least one portion of said rotor contacting said cavity between said inlet means and said exhaust means;

whereby fluid passing through said inlet means and into said cavity is prevented from accessing said exhaust means by passing around a side of said rotor closest to said seal point;

wherein said rotor includes a recess adjacent each vane, each said recess having a contour which can receive an adjacent said vane therein when said vane is pivoted about said pivotable attachment means; and wherein said pivotable attachment means includes a hinge interposed between at least one of said vanes and said trunk, said hinge including means to apply a force causing extension of said vane out of an adjacent said recess, each said vane having a cross-sectional area which is larger away from said hinge than near said hinge.

6. The handpiece of claim 5 wherein said inlet means includes a plurality of inlet ports passing through said cavity, said inlet ports in fluid communication through said housing with the source of elevated pressure compressible fluid in fluid communication with said housing.

7. The handpiece of claim 6 wherein said outlet means includes a plurality of outlet ports passing through said cavity, said outlet ports in fluid communication with a region having lower pressure than said source of elevated pressure compressible fluid, said outlet ports oriented on a side of said seal point opposite said inlet ports around a side of said cavity including said seal point and spaced from each other on a side of said cavity opposite said seal point by an angular displacement, with reference to said central axis of said cavity, by an angle not less than 360° divided by a number of said vanes extending from said trunk;

whereby compressible fluid is prevented from passing from said inlet ports to said outlet ports directly without rotor rotation taking place.

8. The handpiece of claim 7 wherein said hollow cavity has an inside wall which exhibits a radius of curvature adjacent said seal point greater than a radius of said rotor when said vanes are collapsed against said trunk, and wherein said vanes include tips distant from said hinge, said tips of said vanes positioned to allow contact with said wall of said cavity at all times, whereby compressible fluid is prevented from passing from said inlet ports to said outlet ports without rotor rotation.

9. The handpiece of claim 8 wherein said hollow cavity is defined by an insert nested within said housing, said housing formed substantially as a cylinder, said insert having an outer diameter less than an inside diameter of said housing, said housing including a plurality of divider walls dividing a region between said housing and said insert into a high pressure chamber and a low pressure chamber, said high pressure chamber oriented adjacent said inlet ports of said cavity and said low pressure chamber oriented adjacent said exhaust ports of said cavity, said high pressure chamber in fluid communication with an entrance into said housing and said low pressure chamber in fluid communication with an outlet out of said housing, said entrance in communication with the source of elevated pressure compressible fluid;

whereby the elevated pressure compressible fluid leaves the source of elevated pressure compressible fluid, passes through said entrance into said housing, through said inlet ports, around said rotor on a side of said rotor opposite said seal point causing said rotor to rotate, out of said exhaust ports, into said low pressure chamber, and exits said housing through said outlet, thereby converting elevated pressure compressible fluid into a combination of low pressure compressible fluid and rotor rotation.

10. The handpiece of claim 8 wherein said trunk of said rotor includes a plurality of posts extending from said trunk, each said post including one of said hinges, each said vane having a shape which allows said vane to be pivoted into an adjacent said recess;

said cavity including a substantially flat circular end wall with a center thereof oriented along said central axis of said cavity, said end wall including a circular bearing therein at said center thereof sized to receive one end of said rotor at a point oriented along said central axis of said rotor, such that said rotor is supported within said bearing, said bearing is offset from said central axis of said cavity of said insert but said bearing is aligned with a central axis of said housing;

said rotor coupled to said output shaft on another end thereof opposite said one end, said output shaft rotatably supported at a point spaced an amount from said central axis of said cavity similar to an amount of spacing between said central axis of said cavity and said bearing within said end wall; and said output shaft rigidly attached to said trunk of said rotor, whereby when said rotor rotates, said output shaft and said prophylaxis cup are caused to rotate.

11. A disposable dental prophylaxis handpiece, comprising in combination:

a housing;

a fluid reaction device receiving fluid as input and having a rotating shaft as an output, the fluid reaction device including a rotor having a substantially rigid trunk, a plurality of vanes, and a means to pivotably attach said vanes to said trunk, a hollow cavity, said cavity including means to inlet fluid into said cavity, means to exhaust fluid out of said cavity, and means to rotatably support said trunk of said rotor within said cavity;

a prophylaxis cup;

coupling means from said cup to said rotating shaft such that rotation of said shaft rotates said prophylaxis cup;

said rotating shaft output coupled to said rotor such that when fluid enters said cavity, said shaft is caused to rotate;

wherein said rotor includes a recess adjacent each vane, each said recess having a contour which can receive an adjacent said vane therein when said vane is pivoted about said pivotable attachment means; and wherein said pivotable attachment means includes a hinge interposed between at least one of said vanes and said trunk, said hinge including means to apply a force causing extension of said vane out of an adjacent said recess, each said vane having its center of mass spaced from said hinge and moving about an arc a fixed distance from said hinge causing said vane to act both as a flywheel and speed governor whereby the vane provides high torque at low speed.

12. A method for utilizing high pressure compressible fluid to cause a dental prophylaxis device to rotate, including the steps of:

forming a rotor to include a trunk and a plurality of vanes;

connecting each vane through a hinge to the trunk, the hinge allowing each said vane to pivot with respect to the trunk between a first collapsed position and a second extended position;

forming each vane with a mass center spaced from its hinge connection providing both a governor and flywheel effect extracting from the high pressure fluid high torque at low speed;

orienting the rotor within a hollow cavity;

providing an inlet fluid port passing into the cavity;

providing an outlet fluid port passing into the cavity;

coupling the rotor to a means to transmit rotational energy from the rotor to the dental prophylaxis device;

coupling the inlet fluid port to a source of fluid; and directing fluid from the source of fluid through the inlet fluid port and into contact with the vanes of the rotor, causing the rotor and the dental prophylaxis device to rotate;

including the further step of forcing the vanes toward the second position about the hinge such that the vanes are biased away from the trunk unless a greater force is applied against the vanes, causing the vanes to pivot toward the first position adjacent the trunk.

13. The method of claim 12 including the further step of providing a recess in the trunk for each vane, the recess sized to receive the vanes therein when said vanes are pivoted into said first position.

14. The method of claim 13 including the further step of regulating a speed of said rotor by:

shaping said cavity with a circular cross-section; and sizing said cavity with a diameter less than a diameter scribed by tips of the vanes most distant from the trunk when the vanes are in the second position, such that the vanes can contact the cavity at all times where frictional forces increase with increasing velocity and increasing pressure.

15. The method of claim 14 including the further step of offsetting the rotor within the cavity such that at least one of the vanes of the rotor can be in contact with the cavity when the vane is in the first position adjacent the trunk, defining a seal point between the rotor and the cavity which remains at a substantially constant location upon the cavity; and locating the inlet and the outlet on opposite sides of the seal point;

whereby fluid passing into said cavity through the inlet is caused to rotate around the rotor on a side of the rotor spaced from the seal point and then to the outlet, causing the rotor and the dental prophylaxis device to rotate.

16. A dental prophylaxis handpiece, comprising in combination:

a fluid reaction device having a substantially constant velocity rotational output for imparting rotation;

a prophylaxis cup;

said fluid reaction device including a rotor having a trunk, vanes and hinge means between said trunk and said vanes to pivot said vanes between a first position and a second position;

a wall surrounding said rotor;

said first position defined by said vanes collapsed adjacent said trunk with a portion of said vanes abutting said wall;

said second position defined by said vanes pivoted away from said trunk with a portion of said vanes abutting said wall;

said hinge means including a biasing means to apply a force causing extension of said vanes adjacent said wall;

said rotor trunk, hinge and vanes formed from plastic, said vanes having a mass which increases as it extends from said hinge;

an inlet passing through said wall coupled to a source of fluid;

an outlet passing through said wall; and an output means interposed between said rotor and said prophylaxis cup.

17. The device of claim 16 wherein said wall is substantially circular in cross-section and has a central axis at a geometric center thereof, said wall including means to rotatably support said rotor therein with a rotational axis of said rotor offset from and parallel to said central axis of said wall.

18. The device of claim 17 wherein a seal point is provided between said wall and said rotor at a point along said wall closest to said rotational axis of said rotor, said seal point located along said wall at a point not including said inlet or said outlet.

19. The device of claim 18 wherein said inlet and said outlet are positioned such that said vanes of said rotor pass said seal point, said inlet and said outlet in sequence, said rotational axis of said rotor oriented sufficiently close to said wall to cause said vanes to be oriented in said first position when said vanes pass said seal point and to allow said vanes to contact said cylindrical wall when said vanes pass a point on said wall opposite said seal point with said vanes in said second position.

20. The device of claim 19 wherein said vanes on said rotor are spaced from each other by a distance determined by and less than an amount of spacing between said inlet and said outlet, on a side of said wall opposite said seal point, whereby fluid is prevented from passing between said inlet and said outlet without rotor motion.

* * * * *